US012605098B2

(12) United States Patent
Fang et al.

(10) Patent No.: US 12,605,098 B2
(45) Date of Patent: Apr. 21, 2026

(54) EEG HEADBAND WITH IMPROVED AMPLIFIER ATTACHMENT SHAPE CONFORMITY, ELECTRODE PLACEMENT, AND GEL DELIVERY FUNCTIONALITY

(71) Applicant: Natus Medical Incorporated, Middleton, WI (US)

(72) Inventors: Yen Chi Fang, Irvine, CA (US); Satish Ponugoti, Lynwood, WA (US); Stephen Montgomery, Galway (IE)

(73) Assignee: Natus Medical Incorporated, Middleton, WI (US)

( * ) Notice: Subject to any disclaimer, the term of this patent is extended or adjusted under 35 U.S.C. 154(b) by 0 days.

(21) Appl. No.: 19/318,551

(22) Filed: Sep. 4, 2025

(65) Prior Publication Data

US 2026/0076604 A1    Mar. 19, 2026

Related U.S. Application Data

(60) Provisional application No. 63/696,601, filed on Sep. 19, 2024.

(51) Int. Cl.
*A61B 5/291*    (2021.01)
*A61B 5/00*    (2006.01)
*A61B 5/256*    (2021.01)

(52) U.S. Cl.
CPC .............. *A61B 5/291* (2021.01); *A61B 5/256* (2021.01); *A61B 5/6814* (2013.01);
(Continued)

(58) Field of Classification Search
CPC ....... A61B 5/256; A61B 5/291; A61B 5/6814; A61B 5/6831
See application file for complete search history.

(56) References Cited

U.S. PATENT DOCUMENTS 3,602,216 A    8/1971    Moe
4,683,892 A    8/1987    Johansson et al.
(Continued)

FOREIGN PATENT DOCUMENTS

AU    2016354596 A1    6/2018
CN    109009100 B    12/2018
(Continued)

*Primary Examiner* — Eun Hwa Kim
(74) *Attorney, Agent, or Firm* — Daniel C. Pierron; Widerman Malek, PL

(57) ABSTRACT

Systems and methods for electroencephalography headband apparatuses including a strap member, an amplifier device, and electrode assemblies each including a capsule receiving structure having a detent feature configured to resist rotation of a gel capsule positioned there within, a stabilization structure having a central attachment section and a plurality of leg members positioned radially outward from a central axis of the electrode assembly, and a gel delivery structure configured to be positioned at least partially within the capsule receiving structure and to rotatably attach to the stabilization structure such that the gel delivery structure may be able to rotate independently of the stabilization structure. The gel delivery structure may include a plurality of teeth members configured to engage with and lacerate a lower surface of the gel capsule and a plurality of gel delivery channels configured to deliver gel from the gel capsule to patient scalp.

21 Claims, 9 Drawing Sheets

(52) U.S. Cl.
 CPC .... *A61B 5/6831* (2013.01); *A61B 2560/0468*
 (2013.01); *A61B 2562/043* (2013.01); *A61B*
 *2562/14* (2013.01)

(56) References Cited

U.S. PATENT DOCUMENTS

| | | | |
|---|---|---|---|
| 5,273,037 | A | 12/1993 | Itil et al. |
| 6,640,122 | B2 | 10/2003 | Manoli et al. |
| 8,548,555 | B2 | 10/2013 | Jin et al. |
| 8,805,470 | B2 | 8/2014 | Afanasewicz et al. |
| 9,408,575 | B2 | 8/2016 | Bordoley et al. |
| 9,820,670 | B2 | 11/2017 | Parvizi et al. |
| 10,188,307 | B2 | 1/2019 | Henson et al. |
| 10,433,756 | B1 | 10/2019 | Bachelder et al. |
| 10,722,134 | B2 | 7/2020 | Watson et al. |
| 10,888,240 | B2 | 1/2021 | Parvizi et al. |
| 10,898,137 | B2 | 1/2021 | Sargent et al. |
| 11,241,182 | B1 * | 2/2022 | Willis ................... A61B 5/266 |
| 11,241,183 | B2 | 2/2022 | Leuthardt et al. |
| 11,266,476 | B1 | 3/2022 | Willis et al. |
| 11,324,429 | B2 | 5/2022 | Willis et al. |
| 11,357,434 | B2 | 6/2022 | Bachelder et al. |
| 11,520,404 | B2 | 12/2022 | Aimone et al. |
| 11,647,936 | B2 | 5/2023 | Nishiwaki et al. |
| 12,150,769 | B2 | 11/2024 | Parvizi et al. |
| 12,324,670 | B2 | 6/2025 | Parvizi et al. |
| 12,336,826 | B2 | 6/2025 | Parvizi et al. |
| 2015/0257674 | A1 * | 9/2015 | Jordan ................... A61B 5/291 |
| | | | 600/383 |
| 2017/0281036 | A1 * | 10/2017 | Parvizi ................... A61B 5/721 |
| 2019/0200925 | A1 | 7/2019 | Aimone et al. |
| 2025/0213165 | A1 | 7/2025 | Parvizi et al. |

FOREIGN PATENT DOCUMENTS

| | | | | |
|---|---|---|---|---|
| CN | 111419228 | A * | 7/2020 | ............ A61B 5/639 |
| CN | 114366128 | A | 4/2022 | |
| GB | 2591576 | A * | 8/2021 | ............ H01R 24/00 |
| JP | 2016530897 | A | 10/2016 | |
| KR | 20040031950 | A | 4/2004 | |
| WO | 2020159906 | A1 | 8/2020 | |

* cited by examiner

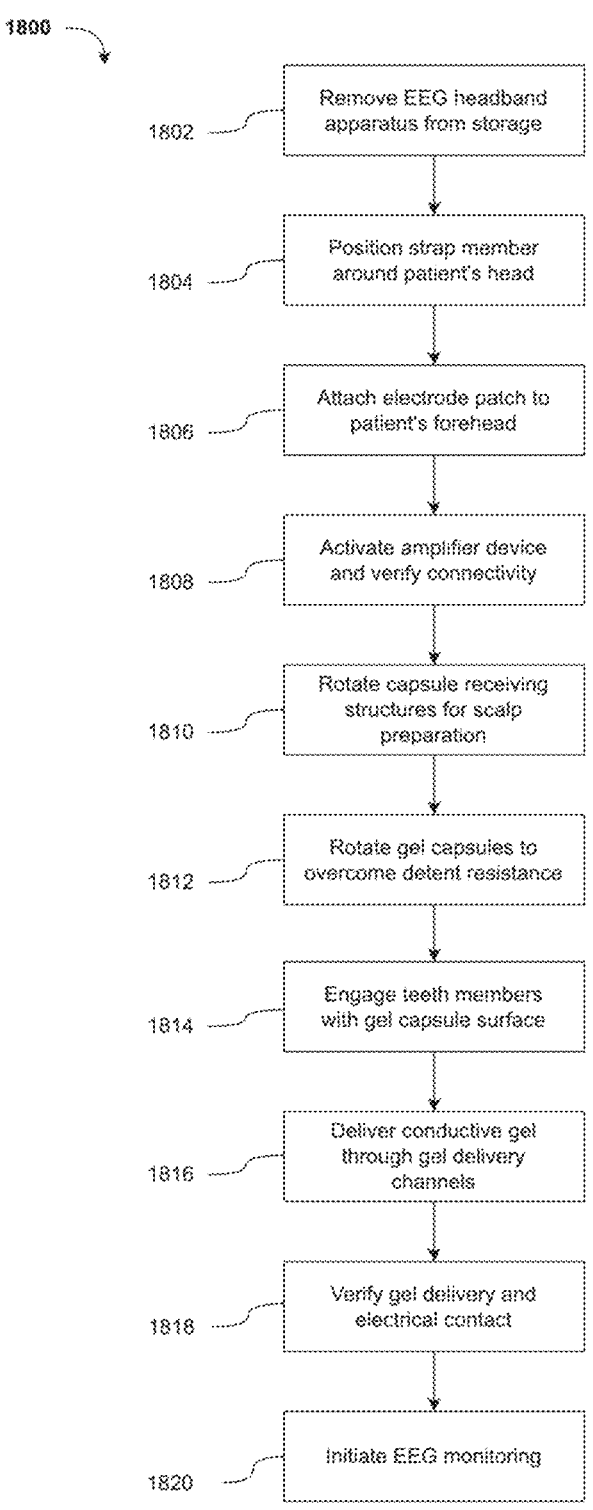

1800

1802 — Remove EEG headband apparatus from storage

1804 — Position strap member around patient's head

1806 — Attach electrode patch to patient's forehead

1808 — Activate amplifier device and verify connectivity

1810 — Rotate capsule receiving structures for scalp preparation

1812 — Rotate gel capsules to overcome detent resistance

1814 — Engage teeth members with gel capsule surface

1816 — Deliver conductive gel through gel delivery channels

1818 — Verify gel delivery and electrical contact

1820 — Initiate EEG monitoring

FIG. 18

EEG HEADBAND WITH IMPROVED AMPLIFIER ATTACHMENT SHAPE CONFORMITY, ELECTRODE PLACEMENT, AND GEL DELIVERY FUNCTIONALITY

RELATED APPLICATIONS

This application claims priority under 35 U.S. C. § 119(e) of U.S. Provisional Patent Application Ser. No. 63/696,601 filed on Sep. 19, 2024 and titled EEG Headband with Improved Amplifier Attachment Shape Conformity, Electrode Placement, and Gel Delivery Functionality. The content of this application is incorporated herein by reference.

FIELD OF THE INVENTION

The present invention relates to a headband apparatus for electroencephalography (EEG).

BACKGROUND OF THE INVENTION

Electroencephalography (EEG) headbands have become increasingly popular for non-invasive brain monitoring in various applications, including medical diagnostics, brain-computer interfaces, and consumer-grade cognitive assessment. These devices rely on precise electrode placement and optimal electrical contact with the scalp to capture the subtle electrical signals generated by neural activity. However, two significant challenges persist in the field: effectively preparing the scalp surface for optimal electrode contact and efficiently delivering conductive gel to ensure reliable signal acquisition.

Scalp preparation presents numerous technical difficulties that can compromise EEG signal quality. The human scalp naturally accumulates oils, dead skin cells, and other debris that create barriers to electrical conductivity between electrodes and the underlying tissue. Hair further complicates electrode placement and contact, as it can physically separate electrodes from the scalp surface and trap contaminants. Traditional preparation methods often involve manual abrasion of the scalp surface, which can be time-consuming, uncomfortable for patients, and inconsistent in effectiveness. Additionally, achieving uniform preparation across multiple electrode sites while maintaining patient comfort remains a persistent challenge in the field.

Conductive gel delivery represents another area of ongoing difficulty in EEG headband design. Conductive gels are commonly used to improve electrical contact between electrodes and the scalp, but their application through hair and onto prepared skin surfaces can be problematic. Current delivery methods often result in uneven gel distribution, with some areas receiving insufficient gel while others may receive excess amounts that can migrate and create unwanted electrical bridges between adjacent electrodes. The timing of gel application relative to scalp preparation and electrode positioning also affects overall system performance, as premature application may interfere with surface preparation while delayed application can allow prepared surfaces to recontaminate.

The piercing mechanism used to access conductive gel containers in existing systems may present additional challenges for user operation. Traditional single-point piercing systems often require substantial rotational force from the user, which can be difficult to apply consistently, particularly when multiple electrodes need to be activated simultaneously. This high force requirement may lead to user fatigue, inconsistent gel release, or potential damage to the gel container or electrode assembly. Furthermore, the sudden release of pressure when a single piercing point penetrates the container membrane can result in uncontrolled gel flow, leading to waste or contamination of adjacent electrode sites.

A multi-tooth piercing mechanism may address these operational challenges by distributing the piercing action across multiple contact points. In such a system, the teeth may be arranged at different longitudinal positions along the piercing mechanism, creating a staggered engagement pattern as the user rotates the electrode assembly. This staggered approach may allow each tooth to engage the container membrane sequentially rather than simultaneously, reducing the peak force required at any given moment during the twisting operation. The distributed piercing action may also provide more controlled gel release, as the membrane is compromised gradually rather than through a single catastrophic failure point.

The sequential engagement of multiple piercing teeth may further enhance user experience by providing tactile feedback during the activation process. As each tooth engages the container membrane, the user may experience a slight reduction in rotational resistance, indicating successful piercing and progression through the activation sequence. This feedback mechanism may help users determine when sufficient rotation has been applied to ensure complete gel access while avoiding over-rotation that could damage the system or cause excessive gel discharge.

Existing EEG headband solutions typically address these challenges through separate, sequential processes that may not be well-integrated. Many current systems rely on manual preparation steps followed by separate gel application, which can be labor-intensive and may not provide consistent results across different users or applications. Some automated systems have been developed, but these often focus on addressing only one aspect of the preparation process while leaving other challenges unresolved. The lack of integrated solutions that can simultaneously address scalp preparation and gel delivery while maintaining electrode stability and patient comfort represents a gap in current technology.

Another challenge that may arise in EEG headband systems is the unintentional rotation of electrode assemblies before intended deployment. Such undesired rotation can occur during handling, transport, or positioning of the headband apparatus, potentially leading to premature activation of the gel release mechanism. When electrode assemblies rotate inadvertently, the piercing mechanism may engage with gel containers before the user intends to deploy the conductive gel, resulting in unwanted gel discharge that can compromise the effectiveness of the electrode system. This premature gel release may also lead to contamination of adjacent electrode sites or waste of the conductive medium. To address this issue, there may be a need for features that inhibit undesired rotation of electrode assemblies, ensuring that gel deployment occurs only when specifically intended by the user. Such rotation-inhibiting mechanisms may help maintain the integrity of the gel delivery system and prevent accidental activation during routine handling of the EEG headband apparatus.

Recent developments in EEG headband technology have begun to address these limitations through more integrated approaches that combine scalp preparation, gel delivery, and electrode stabilization into unified systems. These advances focus on providing automated or semi-automated solutions that can improve consistency, reduce preparation time, and enhance patient comfort while maintaining or improving signal quality compared to traditional methods.

Amplifier attachment and support present additional considerations in EEG headband design that may significantly impact both signal quality and patient comfort. The amplifier device, which processes and transmits the electrical signals captured by the electrode assemblies, may need to maintain stable positioning relative to the patient's head while accommodating the natural variations in head shape and size across different users. Traditional rigid mounting systems may create pressure points or gaps that can compromise both comfort and electrical performance during extended monitoring sessions.

The conformability of amplifier attachment systems may be addressed through flexible mounting arrangements that can adapt to individual head contours. Such systems may utilize flexible backing members that can deform to match the curvature of the patient's head while maintaining sufficient structural integrity to support the amplifier device. The backing member may distribute the weight and pressure of the amplifier across a larger surface area, reducing localized stress concentrations that could cause discomfort or skin irritation. This distributed support approach may also help maintain consistent contact between the headband and the patient's head, which can be important for maintaining stable electrode positioning throughout the monitoring period.

The backing member may serve multiple functions beyond simple weight distribution. It may provide a stable platform that resists movement of the amplifier device relative to the electrode assemblies, which can help maintain consistent electrical connections and reduce motion artifacts in the recorded signals. The backing member may also act as a buffer between the rigid amplifier housing and the patient's skin, providing a more comfortable interface that can accommodate minor movements without creating pressure points or allowing the device to shift position.

Attachment mechanisms between the amplifier device and the backing member may be designed to allow for easy installation and removal while maintaining secure connection during use. Such mechanisms may include magnetic attachment systems, mechanical fasteners, or interference fit arrangements that can accommodate the flexibility of the backing member while providing reliable retention of the amplifier device. The attachment system may also be configured to allow for some degree of adjustment in the amplifier position relative to the backing member, enabling fine-tuning of the device placement for optimal comfort and performance on different patients.

The material properties of the backing member may be selected to provide appropriate flexibility while maintaining durability and biocompatibility. The backing member may be formed from materials that can flex and conform to head contours without permanent deformation, allowing the device to be reused across multiple patients with different head shapes. The surface characteristics of the backing member may also be designed to provide appropriate friction against the patient's skin or hair to help maintain headband position without causing discomfort or skin irritation.

This background information is provided to reveal information believed by the applicant to be of possible relevance to the present invention. No admission is necessarily intended, nor should be construed, that any of the preceding information constitutes prior art against the present invention.

SUMMARY OF THE INVENTION

The present disclosure provides an electroencephalography (EEG) headband apparatus. The apparatus may include a strap member configured to be removably attachable to a head of a patient, an amplifier device attached to the strap member, and a plurality of electrode assemblies attached to the strap member. Each electrode assembly of the plurality of electrode assemblies may include a capsule receiving structure having a detent feature configured to resist rotation of a gel capsule positioned therewithin, a stabilization structure, and a gel delivery structure. The stabilization structure may include a central attachment section and a plurality of leg members positioned radially outward from a central axis of the electrode assembly. The gel delivery structure may be configured to be positioned at least partially within the capsule receiving structure and to rotatably attach to the stabilization structure such that the gel delivery structure may be able to rotate independently of the stabilization structure. The gel delivery structure may include a plurality of teeth members configured to engage with and lacerate a lower surface of the gel capsule, and a plurality of gel delivery channels configured to deliver gel from the gel delivery capsule to a skin surface of the head of the patient.

In some embodiments, the capsule receiving structure may include a threaded inner surface configured to engage with threads comprised by the gel capsule to facilitate the positioning and attachment of the gel capsule to the capsule receiving structure.

In other embodiments, a first tooth of the plurality of teeth members may be configured to have a top point thereof at a first longitudinal position, and a second tooth of the plurality of teeth members may be configured to have a top point thereof at a second longitudinal position. The first longitudinal position may be such that the first tooth engages with the lower surface of the gel capsule before the second tooth. Rotation of the gel capsule may cause translation of the gel capsule along a central axis of the electrode assembly, thereby causing the lower surface thereof to engage with the first tooth and subsequently engage with the second tooth as the gel capsule translates along the central axis.

In some embodiments, the plurality of gel delivery channels may each include an abrading tip configured to abrade the skin surface of the head of the patient.

In other embodiments, a lower end of the plurality of gel delivery channels may extend further in a downward direction than a lower end of the plurality of leg members.

In some embodiments, the detent feature may be a raised section on an inner surface of the capsule receiving structure that is configured to interface with a structure of the gel capsule to resist rotation of the gel capsule.

In other embodiments, the stabilization structure may be fixedly attached to the strap member and may include an attachment member. The gel delivery structure may include a deflectable attachment member configured to engage with the attachment member of the stabilization structure to rotatably attach the gel delivery structure to the stabilization structure.

In some embodiments, the apparatus may further include a flexible backing member fixedly attached to the strap member on a side of the strap member opposite a side of the strap member to which the amplifier device is attached and including a plurality of backing member attachment members. The amplifier device may include a plurality of amplifier device attachment members configured to removably attach to the backing member attachment members to removably attach the amplifier device to the flexible backing member, thereby attaching the amplifier device to the strap member.

BRIEF DESCRIPTION OF THE DRAWINGS

FIG. 18 is a flowchart illustrating a method of deploying the EEG headband apparatus according to an embodiment of the invention.

DETAILED DESCRIPTION OF THE INVENTION

Figure 1:
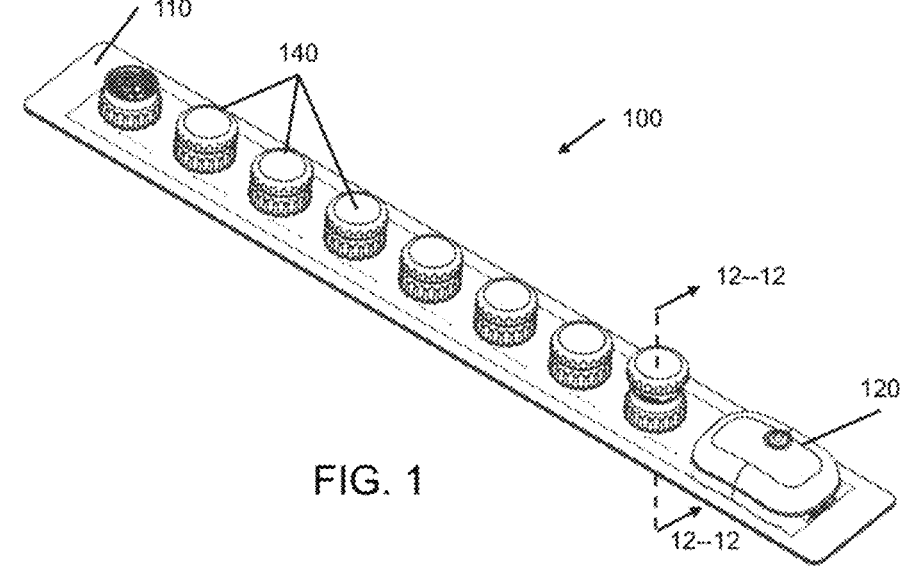
FIG. 1 is an upper perspective view of an EEG headband apparatus according to an embodiment of the invention.
Figure 2:
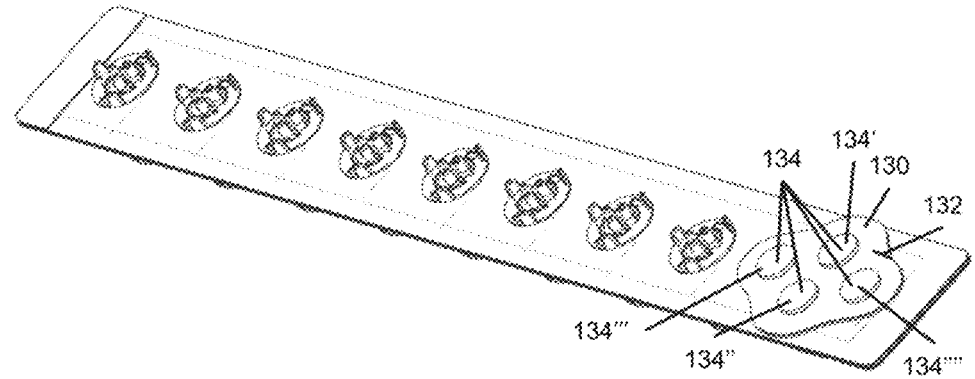
FIG. 2 is a lower perspective view of the EEG headband apparatus of FIG. 1.
Figure 3:
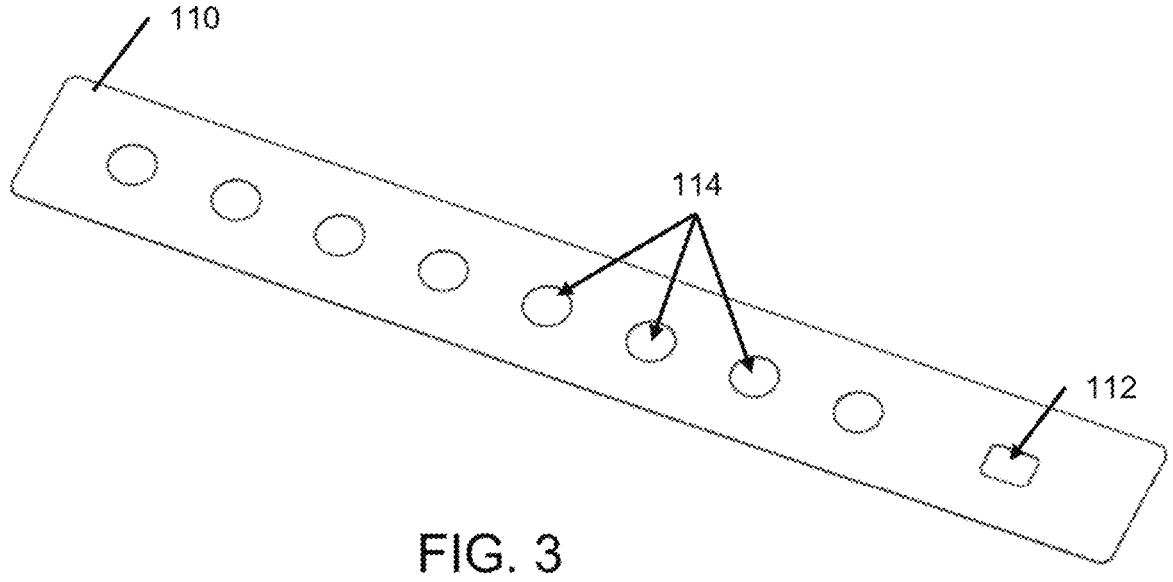
FIG. 3 is a perspective view of strap member of the EEG headband apparatus of FIG. 1.
Figure 4:
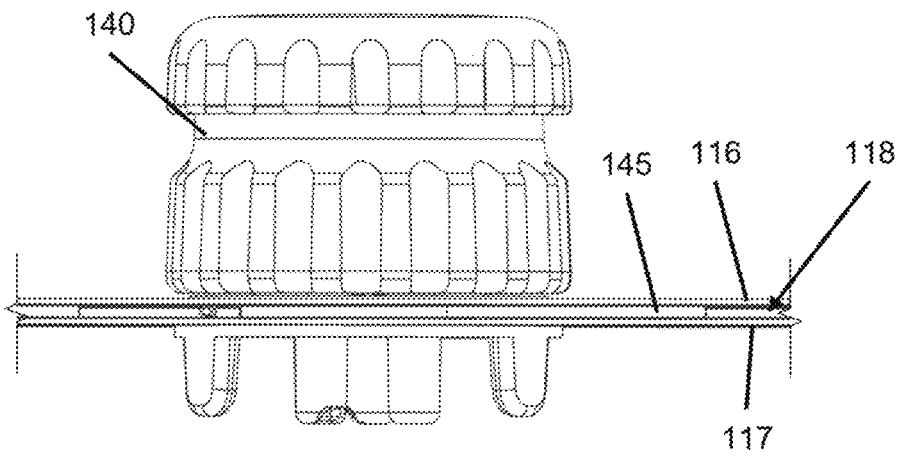
FIG. 4 is a side view of an electrode assembly and the strap member of the EEG headband apparatus of FIG. 1.

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Those of ordinary skill in the art realize that the following descriptions of the embodiments of the present invention are illustrative and are not intended to be limiting in any way. Other embodiments of the present invention will readily suggest themselves to such skilled persons having the benefit of this disclosure. Like numbers refer to like elements throughout.

Although the following detailed description contains many specifics for the purposes of illustration, anyone of ordinary skill in the art will appreciate that many variations and alterations to the following details are within the scope of the invention. Accordingly, the following embodiments of the invention are set forth without any loss of generality to, and without imposing limitations upon, the invention.

In this detailed description of the present invention, a person skilled in the art should note that directional terms, such as "above," "below," "upper," "lower," and other like terms are used for the convenience of the reader in reference to the drawings. Also, a person skilled in the art should notice this description may contain other terminology to convey position, orientation, and direction without departing from the principles of the present invention.

Furthermore, in this detailed description, a person skilled in the art should note that quantitative qualifying terms such as "generally," "substantially," "mostly," and other terms are used, in general, to mean that the referred to object, characteristic, or quality constitutes a majority of the subject of the reference. The meaning of any of these terms is dependent upon the context within which it is used, and the meaning may be expressly modified.

An embodiment of the invention, as shown and described by the various figures and accompanying text, provides a headband apparatus operable for performing EEG observation of a patient. Referring now to FIGS. 1-10, an embodiment of a headband apparatus 100 is presented. The headband apparatus 100 may be removably attachable to the head of a patient and configured to position EEG electrodes proximate to the skin of the patient to facilitate conducting an EEG analysis of the patient. The headband apparatus 100 may be configured to enable preparing the skin surface of the patient, dispensing of conductive gel, and maintaining its position on the head of the patient for the EEG analysis. The headband apparatus 100 may comprise a strap member 110, an amplifier device 120, and a plurality of electrode assemblies 140. The amplifier device 120 may be attachable to the strap member 110 at a first location. The plurality of electrode assemblies 140 may be attachable to the strap member 110 at a variety of locations distributed along a length of the strap member 110.

The strap member 110 may be an elongate structure or material configured to facilitate attachment of the amplifier device 120 and the plurality of electrode assemblies 140 as described above. The strap member 110 may comprise a first cutout 112 configured to facilitate attachment of the amplifier device 120 and a plurality of second cutouts 114, each cutout of the plurality of second cutouts 114 being configured to facilitate the attachment of an electrode assembly of the plurality of electrode assemblies 140. The strap member 110 may be formed of one or more flexible materials to permit the strap member 110 to be wrapped around the patient head. Additionally, the strap member 110 may be formed of an elastic material or any other material that may be stretched to be attached to the patient head to minimize relative movement between the headband apparatus 100 and the patient head without permanently deforming the strap member 110. In some embodiment, the strap member 110 may be an elastic fabric.

In some embodiments, the strap member 110 may further comprise an upper strap member 116 and a lower strap member 117. The upper and lower strap members 116, 117 may be formed of a flexible, elastic material as described above and each include cutouts 112, 114 that are in alignment so as to form continuous open sections of the strap member 110. The upper and lower strap members 116, 117 may define therebetween a void region 118 within which electrode wires 145 configured to electrically connect each electrode of the plurality of electrode assemblies 140 with the amplifier device 120 may be positioned.

Figure 7:
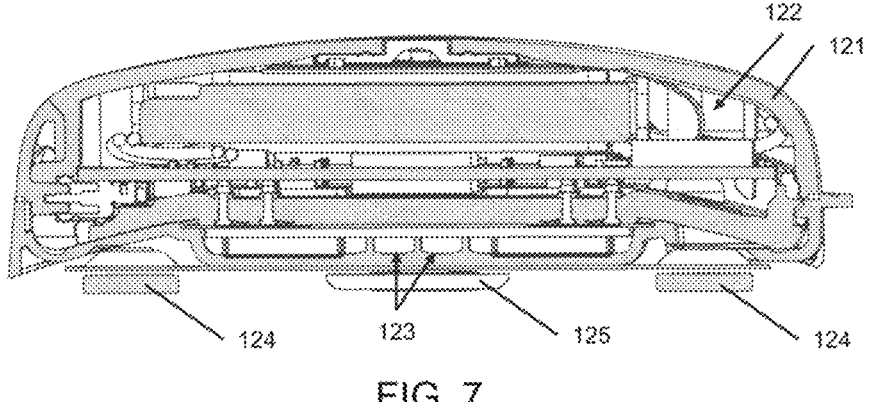
FIG. 7 is a front sectional view of the amplifier device of FIG. 5.

Referring now specifically to FIGS. 5-9, additional aspects regarding the amplifier device 120 will be discussed in greater detail. The amplifier device 120 may be positioned in electrical communication with the plurality of electrode assemblies 140 via the electrode wires 145 mentioned above. The electrode wires 145 may be any type of conductive structure or mechanism that is operable to electrically connect each electrode assembly of the plurality of electrode assemblies 140 with the amplifier device 120, including, bot not limited to, wires, traces, conductive inks, and the like. The amplifier device 120 may comprise an outer housing 121 that defines an interior cavity 122 within which amplifier electronics may be positioned, as shown in FIG. 7. The amplifier electronics may be configured to receive electrical signals from the plurality of electrode assemblies, in some embodiments perform smoothing, noise reduction, or other digital signal processing to produce modified signals, and transmit either the original signals or the modified signals to a remote computerized device. Such transmission may be accomplished by wired transmission (such as by Universal Serial Bus (USB) or Ethernet connection) or by wireless transmission (such as by Bluetooth, Wi-Fi, or any other IEEE 802.XX standard). Such transmission may be across a personal area network, a local area network, or a wide area network, such as the Internet. Accordingly, the amplifier device 120 may comprise a communication device operable to accomplish such transmission. The amplifier device 120 may further comprise a power source, such as a battery, that may provide electrical power to the amplifier electronics and/or to the plurality of electrodes 140 via the electrode wires 145.

The amplifier device 120 may be positioned relative to the strap member 110 so as to be adjacent to the first cutout 112. The first cutout 112 may be configured to permit a plurality of electrode wires 145 to pass there into, with the plurality of electrode wires 145 running into the interior cavity 122 of the amplifier device. There, the plurality of electrode wires 145 may be attached to the amplifier electronics to establish electrical communication between the amplifier device 120 and the plurality of electrode assemblies 140. The outer housing 121 may comprise one or more conduits 123 configured to permit the electrode wires 145 to extend into the inner cavity 122. The amplifier device 120 may further comprise a lower cap member 125 configured to cover the first cutout 112 such that the plurality of electrode wires 145 and the one or more conduits 123 are not exposed. The lower cap member 125 may be releasably attachable to a structure of the amplifier device 120 to permit a user to selectively cover and uncover the conduits 123 to facilitate the positioning and subsequent protection of the plurality of electrode wires 145.

Figures 5, 6:
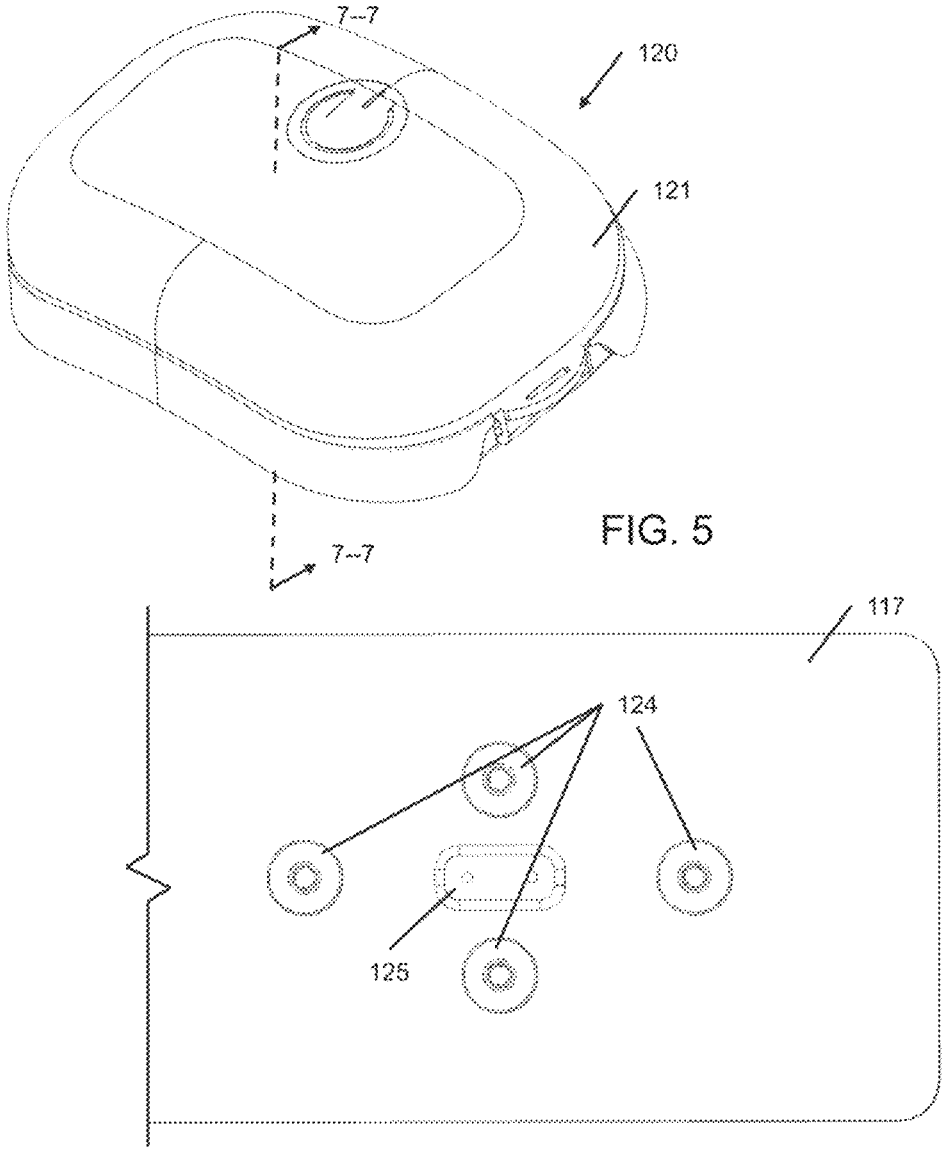
FIG. 5 is a perspective view of an amplifier device of the EEG headband apparatus of FIG. 1.
FIG. 6 is a partial lower view of the EEG headband apparatus of FIG. 1.

As shown in FIG. 6, the amplifier device 120 may comprise a plurality of backing member attachment members 124. The plurality of backing member attachment members 124 may be configured to be positioned on a side of the strap member 140 opposite the outer housing 121. In the present embodiment, the outer housing 121 may be positioned on a side of the strap member 110 adjacent to the upper strap member 116 and the plurality of backing member attachment members 124 may be positioned on a side of the strap member 110 adjacent to the lower strap member 117. Moreover, the outer housing 121 may comprise a plurality of amplifier device attachment members 126 configured to extend downward and be positioned within an area bounded by the backing member attachment members 124, thereby trapping the strap member 110 therebetween. The backing member attachment members 124 may be removably attached to the amplifier device attachment members 126 by at least one of an interference fit and magnetic attraction. The attachment between the backing member attachment members 124 and the amplifier device attachment members 126 may facilitate attachment of the amplifier device 120 to the strap member 110. As shown in FIG. 6, the backing member attachment members 124 may be positioned adjacent to the lower strap member 117 and visible to as well as accessible by a user from below the lower strap member 117. Additionally, the lower cap member 125 may be at least accessible from below the lower strap member 117.

Referring back to FIG. 2, an electrode patch 130 comprised by the headband apparatus 100 will be discussed in greater detail. The electrode patch 130 may be configured to facilitate supporting the amplifier device 120 and attaching the headband apparatus 100 to the patient. In some embodiments, a lower surface 132 of the electrode patch 130 may comprise an adhesive material that may enable the electrode patch 130 to be removably attached to the forehead of the patient. Such removable attachment may enable the electrode patch 130 to at least partially support the weight of the amplifier device 120.

Additionally, the electrode patch 130 may comprise a plurality of electrode patch electrodes 134. Any number of electrodes may be comprised by the plurality of electrode patch electrodes 134. In the present embodiment, the plurality of electrode patch electrodes 134 comprises four electrodes. The number of electrodes may be configured to conform to a known EEG exam system, such as a 10-20 system as is known in the art for conducting an EEG exam. Accordingly, the plurality of electrode patch electrodes may comprise a first electrode 134' configured as a ground connector, a second electrode 134" configured as a reference electrode, a third electrode 134''' configured as a first prefrontal (Fp1) electrode, and a fourth electrode 134'''' configured as a second pre-frontal (Fp2) electrode. The plurality of electrode terminals 134 may be electrically connected to the amplifier electronics similarly to the electrode wires 145.

Figure 8:
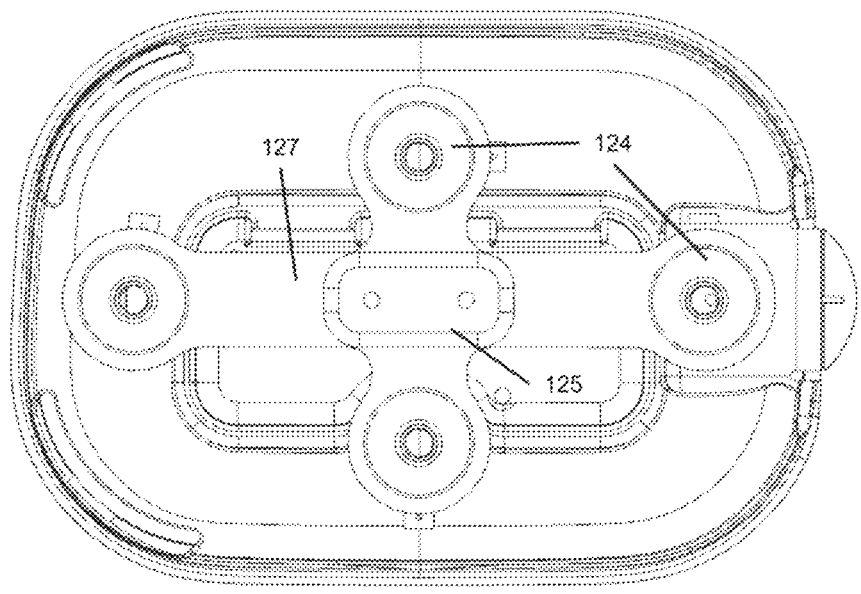
FIG. 8 is a lower view of a backing member and the amplifier device of the EEG headband apparatus of FIG. 1.
Figure 9:
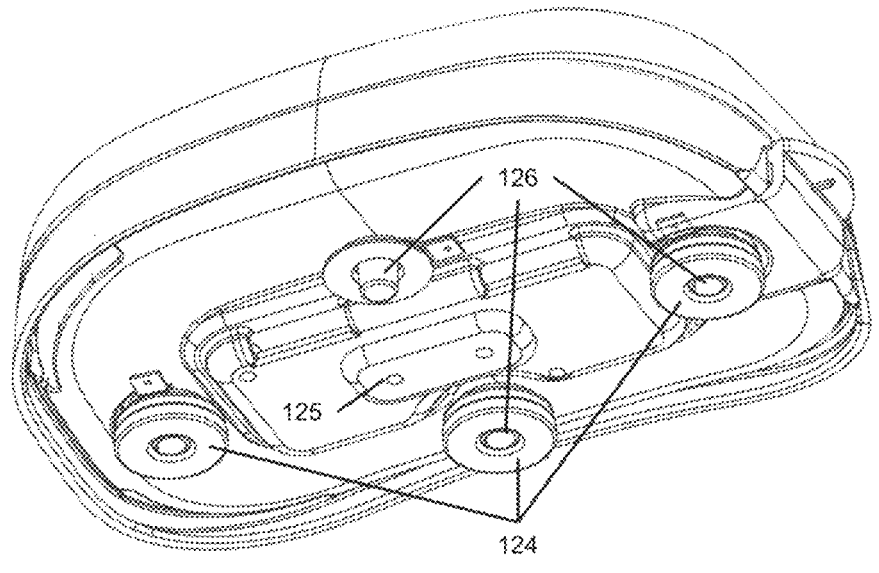
FIG. 9 is a lower perspective view of the amplifier member of FIG. 5.
Figure 10:
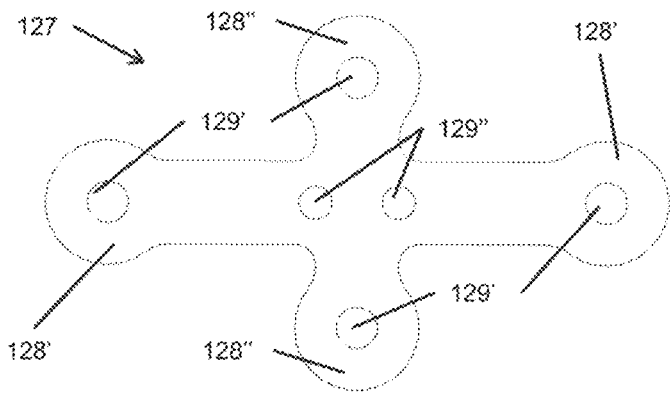
FIG. 10 is a top view of the backing member of the EEG headband apparatus of FIG. 1.

The amplifier apparatus 120 may further comprise a backing member 127, as shown specifically in FIGS. 8 and 10. The backing member 127 may be positionable adjacent to the lower strap member 117 and configured to be retained by one or more of the backing member attachment members 124 and/or the lower cap member 125. The backing member 127 may be configured to provide additional support to the outer housing 121 when the amplifier apparatus 120 is attached to the strap member 110. The backing member 127 may comprise a plurality of arms 128 and a plurality of apertures 129. The plurality of arms 128 and the plurality of apertures 129 may be configured to facilitate attachment and retention of the backing member 127 by the backing member attachment members 124 and/or the lower cap member 125. The plurality of arms 128 may comprise a first set of arms 128' configured to extend along a long axis of the outer housing 121 and a second set of arms 128" to extend along a short axis of the outer housing 121. Each of the arms of the plurality of arms 128 may comprise an aperture of the plurality of apertures 129. Each of the arms of the plurality of arms 128 may have a large, round section at the end configured to approximately conform to the shape of the backing member attachment members 124. Each of the first set of arms 128' and the second set of arms 128" may comprise an aperture 129' configured to conform to the size and shape of the amplifier device attachment member 126, permitting a amplifier device attachment member 126 to pass therethrough and engage with a backing member attachment member 124. The backing member 127 may further comprise two apertures 129" of the plurality of apertures 129 located proximate to the center of the backing member 127 and configured to conform to the shape of the conduits 123 and/or an attachment structure of the lower cap member 125 to permit one or both thereof to pass therethrough.

The backing member 127 may be formed of a flexible material and configured to flex when the headband apparatus 100 is worn by a patient. The backing member 127 may provide support to each of the strap member 110 and the outer housing 121 and reduce the strain therebetween when the headband apparatus 100 is worn by a patient.

The backing member 127 may be formed from various flexible materials that provide both structural support and biocompatibility for patient contact. In some embodiments, the backing member 127 may be formed from medical-grade silicone, which may offer excellent flexibility while maintaining structural integrity and providing biocompatible properties suitable for extended skin contact. The backing member 127 may alternatively be constructed from thermoplastic polyurethane (TPU), which may provide good elasticity and durability while meeting biocompatibility standards for medical devices.

In other embodiments, the backing member 127 may be formed from medical-grade polyethylene, which may offer flexibility and chemical resistance while maintaining biocompatible characteristics. The backing member 127 may also be constructed from ethylene vinyl acetate (EVA), which may provide cushioning properties and flexibility while being suitable for medical applications. Additionally, the backing member 127 may be formed from medical-grade polyvinyl chloride (PVC), which may offer good flexibility and can be formulated to meet biocompatibility requirements.

The backing member 127 may further be constructed from polyether block amide (PEBA), which may provide excellent flexibility and elasticity while maintaining biocompatible properties. In some cases, the backing member 127 may be formed from medical-grade rubber compounds, such as natural rubber latex or synthetic rubber formulations, which may offer flexibility and conformability while meeting biocompatibility standards. The backing member 127 may also be constructed from flexible polyolefin materials, which may provide good chemical resistance and flexibility while being suitable for medical device applications.

In certain embodiments, the backing member 127 may be formed from composite materials that combine multiple flexible substrates, such as fabric-reinforced silicone or polymer-coated textiles, which may provide enhanced structural support while maintaining flexibility and biocompatibility. The selection of material for the backing member 127 may be based on factors such as the required degree of flexibility, durability requirements, sterilization compatibility, and specific biocompatibility standards for the intended application.

Referring now to FIGS. 11-17, the electrode assemblies 140 of the present embodiment will be discussed in greater detail. Each electrode assembly 140 of the plurality of electrode assemblies 140 may comprise a capsule receiving structure 141, a stabilization structure 150, a gel delivery structure 160, and a capsule cap member 170. The capsule receiving structure 141 may be generally configured for receiving and temporarily attaching a gel capsule 180 for use in the invention. The gel comprised by the gel capsule 180 may be configured to facilitate performance of an EEG analysis. In some embodiments, a conductive gel may be comprised by the gel capsule 180. The capsule receiving structure 141 may comprise features and/or structures configured to facilitate removable attached of the gel capsule 180.

In the present embodiment, the capsule receiving structure 141 may comprise a sidewall 142 comprising one or more threads 143 formed on an inner surface thereof. The one or more threads 143 may be configured to engage with one or more threads of the gel capsule 180, thereby removably attaching the gel capsule 180 to the capsule receiving structure 141. Moreover, the sidewall of 142 of the capsule receiving structure 141 may be dimensioned to at least partially position the gel capsule 180 therewithin, which may facilitate the delivery of the gel comprised by the gel capsule 180 via the gel delivery structure 160 to the scalp of the patient. Additionally, the rotation of the gel capsule 180 to engage with the threads 143 of the capsule receiving structure 141 may facilitate the puncturing of a gel packet comprising the gel comprised by the gel capsule 180 as will be discussed in greater detail below. The sidewall 142 may further be configured to have a height h configured to cooperate with a height of the gel capsule 180 to further facilitate delivery of gel via the gel delivery structure 160 by preventing or minimizing the escape of the gel out the top of the electrode assembly 140 instead of through the gel delivery structure 160. Moreover, the capsule cap member 170 may be configured to overlie at least a portion of the sidewall 142 to further inhibit the escape of gel out of the top of the capsule receiving structure 141.

Additionally, the sidewall 142 may further comprise one or more features formed on an outer surface thereof. Such features may be configured to facilitate manipulation of the electrode assembly 140 by a user, both in preparing the scalp surface of the patent and in attachment of the gel capsule 180 to the capsule receiving structure 141. In the present embodiment, the sidewall 142 comprises a plurality of grooves 144 formed in the outer surface to facilitate a user's grip of the outer surface of the sidewall 142. The plurality of grooves 144 may be configured to conform with a plurality of grooves 172 comprised by the capsule cap member 170. The pluralities of grooves 144, 172 may facilitate the positioning of the gel capsule 180 within the gel delivery structure 160 may facilitating rotation of at least one of the sidewall 142 and the capsule cap member 170 to engage the threads 143 with the gel capsule 180. Such engagement with the threads 143 may enable a user to manipulate the capsule cap member 170 to translate the gel capsule 180 along a central/longitudinal axis Ia to dispense the gel contained thereby.

The capsule cap member 170 may be configured to attach to the gel capsule 180 to facilitate the positioning of the gel capsule 180 within the capsule receiving structure 141. In the present embodiment, the capsule cap member 170 comprises a sidewall 171, an upper wall 174, and one or more attachment structures 176. The one or more attachment structures 176 may extend downward from the upper wall 174 and be configured to engage with a structure of the gel capsule 180, such as a gel capsule attachment structure 182, to attach the capsule cap member 170 to the gel capsule 180.

Such attachment between the capsule cap member 170 and the gel capsule 180 may be detachable. The one or more attachment structures 176 may engage with the gel capsule attachment structure 182 by one or both of the structures 176, 182 being deflected by the other as they translate along a longitudinal axis Ia towards each other until each structure snaps into a recess comprised by the other, thereby detachably attaching the capsule cap member 170 and the gel capsule 180.

Figure 17:
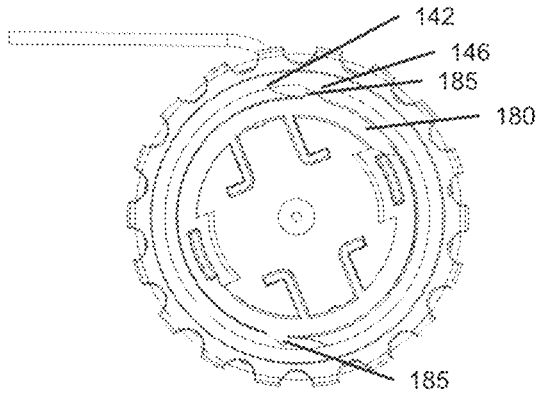
FIG. 17 is a top view of a capsule receiving structure and gel delivery structure of an electrode assembly of the EEG headband apparatus of FIG. 1.

Referring additionally to FIG. 17, the capsule receiving structure 141 may further comprises a detent feature 146. The detent feature 146 may be a raised section of an inner surface of the sidewall 142. The detent feature 146 may be configured to interface with a structure of the gel capsule 180 to resist the rotation of the gel capsule 180. Accordingly, the detent feature 146 may be positioned at a location that, when the detent feature 146 interfaces with the structure, such as a detent interfacing structure 185, of the gel capsule 180, the gel capsule is at a desired location. Such a desired location may be a location associated with pre-delivery of the gel comprised by the gel capsule 180, such that a user may positioned the gel capsule 180 partially within the capsule receiving structure 141 at a location without dispensing the gel comprised by the gel capsule 180, as described herein below. Another desired location may be a location associated with completed delivery of gel comprised by the gel capsule 180.

The interface between the detent feature 146 and the detent interfacing structure 185 may be configured to provide controlled resistance to rotation while allowing for intentional advancement of the gel capsule 180 when sufficient rotational force is applied. The detent interfacing structure 185 may comprise a complementary geometry that engages with the detent feature 146, such as a groove, notch, or recessed area formed in an outer surface of the gel capsule 180. When the detent interfacing structure 185 aligns with the detent feature 146, the raised section of the detent feature 146 may partially extend into or engage with the detent interfacing structure 185, creating a mechanical interference that resists further rotation of the gel capsule 180.

The engagement between the detent feature 146 and the detent interfacing structure 185 may provide tactile feedback to the user, indicating that the gel capsule 180 has reached a predetermined rotational position. The detent feature 146 may be dimensioned to allow the detent interfacing structure 185 to pass over or through the raised section when sufficient rotational force is applied, enabling the gel capsule 180 to advance to subsequent positions along the threaded engagement. The height and profile of the detent feature 146 may be configured to provide appropriate resistance force that can be overcome by normal user operation while preventing inadvertent rotation due to handling or vibration.

In some embodiments, the detent interfacing structure 185 may comprise multiple engagement surfaces or features that correspond to different rotational positions of the gel capsule 180. The detent feature 146 may be configured to engage with each of these surfaces sequentially as the gel capsule 180 is rotated, providing multiple discrete stopping positions during the gel delivery process. The interface may also be designed to allow for bidirectional engagement, permitting the gel capsule 180 to be rotated in either direction while maintaining the resistance characteristics provided by the detent mechanism.

Figures 14, 15, 16:
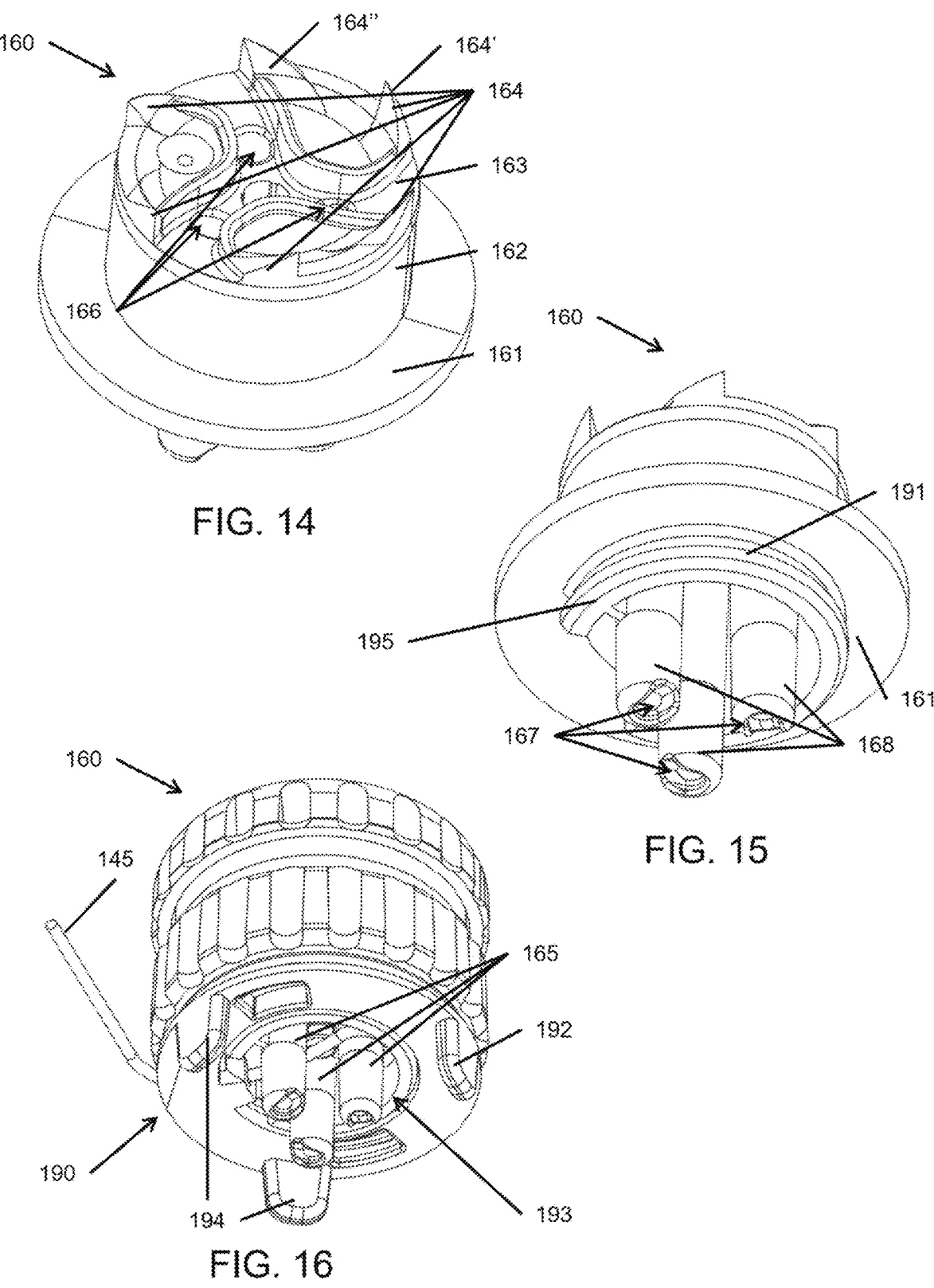
FIG. 14 is a perspective view of a gel delivery structure of an electrode assembly of the EEG headband apparatus of FIG. 1.
FIG. 15 is a lower perspective view of the gel delivery structure of FIG. 14.
FIG. 16 is a lower perspective view of an electrode assembly of the EEG headband apparatus of FIG. 1 in a post-gel delivery position.

Referring additionally to FIGS. 14 and 15, aspects of the gel delivery structure 160 will be discussed in greater detail. The gel delivery structure 160 may be configured to cause the release of gel from the gel capsule 180 and deliver it onto the scalp of the patient. The gel delivery structure 160 may comprise a flange member 161, a center wall 162 extending generally upward from the flange member 161, an upper wall 163, a plurality of teeth members 164 extending upward from the upper wall 163, and a plurality of gel delivery channels 165 extending downward from the upper wall 163 and through a cavity defined by the center wall 162, extending past a plane defined by the flange member 161.

The plurality of teeth members 164 may be configured to engage with and lacerate a lower surface 184 of the gel capsule 180. The lower surface 184 may be formed of a material configured to be lacerated by the plurality of teeth members 164 and release gel contained within a gel cavity 186 of the gel capsule 180, forming a retaining film to keep the gel in the gel cavity 186 until so lacerated. The plurality of teeth members 164 may have any geometry that is operable to lacerate the lower surface 184 as described herein. Additionally, the plurality of teeth member 164 may be configured to have differing geometries such that a first tooth member 164' may engage the lower surface 184 when the gel capsule 180 is at a first longitudinal position along axis Ia and that a second tooth member 164'' may engage the lower surface 184 when the gel capsule 180 is at a second longitudinal position along axis Ia. This may reduce the force needed for the plurality of teeth members 164 to lacerate the lower surface 184 by not having the plurality of teeth members 164 interface with the lower surface 184 simultaneously. In the present embodiment, the first tooth member 164' may have a top point at a first longitudinal position along axis Ia and the second tooth member 164'' may have a top point at a second longitudinal position along axis Ia, such that the top point of the first tooth member 164' engages with the lower surface 184 before the top point of the second tooth member 164''.

The gel delivery channels 165 may be configured to provide a conduit for gel to flow from the gel capsule 180 to the scalp of the patient. Accordingly, the gel delivery channels 165 may be configured to establish fluidic communication between the space above the upper wall 163 to a lower end of the electrode assembly 140. In the present embodiment, the gel delivery channels 165 comprise elongate tubes having upper apertures 166 in the upper wall 163 and lower apertures 167 at a lower end of each tube. Additionally, each gel delivery channel 165 may comprise a tip member 168 at the lower end of the gel delivery channel 165. The tip member 168 may be configured to define an exit aperture 169 of the gel delivery channel 165. In some embodiments, the tip member 168 may be in a defined rotational position. In some embodiments, the tip member 168 may be rotatable respective to a longitudinal axis of the gel delivery channel with which it is associated to change a direction which gel will be ejected therefrom. In some embodiments, the tip member 168 may be configured to have an abrading tip configured to abrade the skin surface of the head of the patient, i.e. the patient scalp. Such rotation may be caused by attachment between the gel delivery structure 160 and the capsule receiving structure 141, such that a user may rotate the capsule receiving structure 141 and thereby simultaneously rotate the gel delivery structure 160. This may cause the gel delivery structure 160 to rotate about axis Ia and cause the tip member 168 of each gel delivery channel 165 to rotate about axis Ia, abrading the scalp of the patient as it rotates.

The upper wall 163 may have a varied geometry, with some portions thereof being at a higher elevation than other parts. Particularly, the upper wall 163 may be sloped towards its center, such that an outer portion of the upper wall 163 may have a greater elevation than the central portion thereof. The upper apertures 166 may be positioned generally towards the central portion of the upper wall 163, increasing the total amount of gel from the gel capsule 180 that may be delivered therethrough. Moreover, such sloping may further inhibit the flow of gel to the space between the gel delivery structure 160 and the sidewall 142. Additionally, such positioning of the upper apertures 166 at a lower elevation from the outer portion of the upper wall 163 may prevent the lower surface 184 of the gel capsule from blocking the flow of gel through the upper apertures 166 after having been lacerated.

Figures 11, 12, 13:
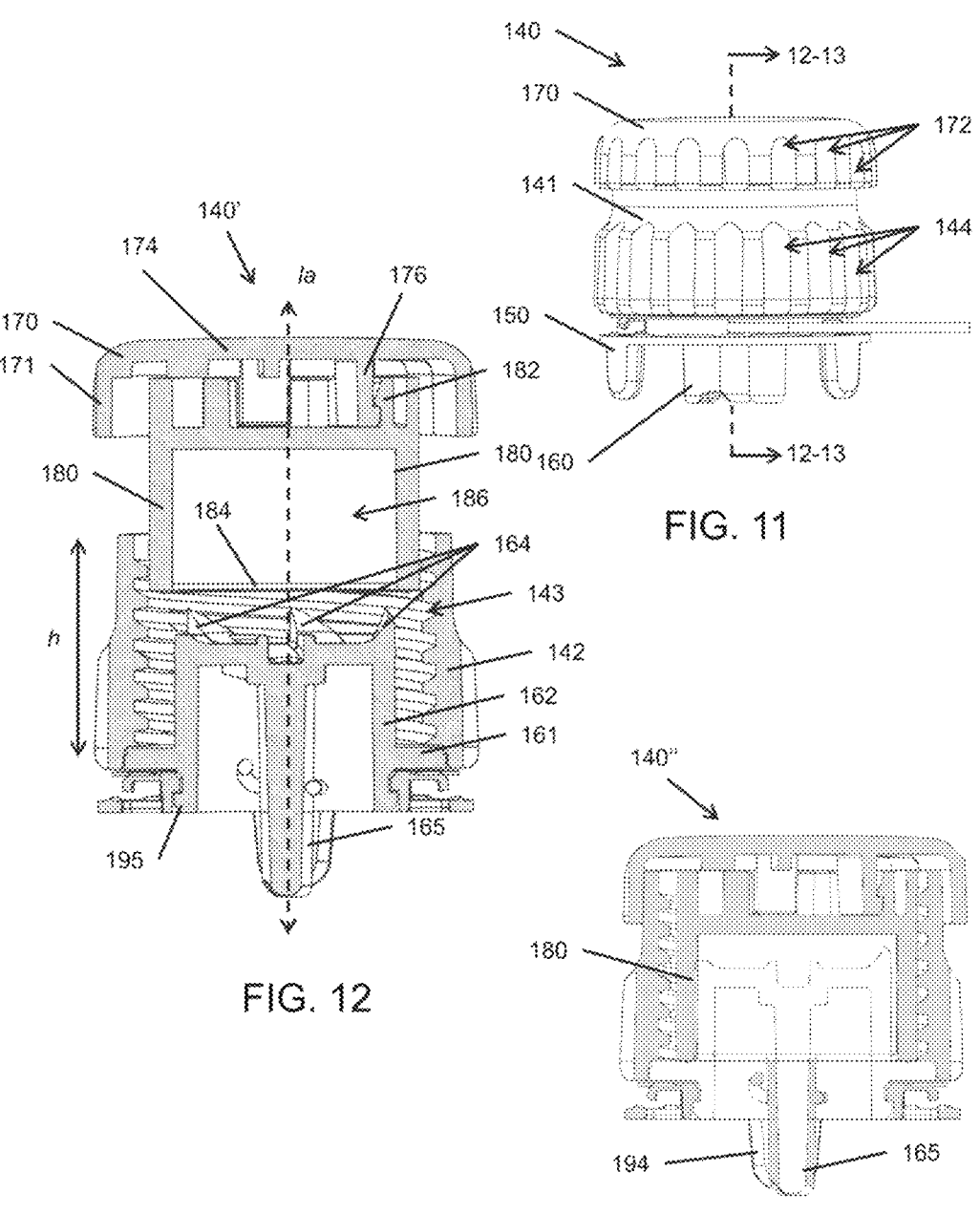
FIG. 11 is a side view of an electrode assembly of the EEG headband apparatus of FIG. 1 in a position where a gel container has been dispensed.
FIG. 12 is a side sectional view of an electrode assembly of the EEG headband apparatus of FIG. 1 where a gel container is in a pre-disposal position.
FIG. 13 is a side sectional view of an electrode assembly of the EEG headband apparatus of FIG. 1 where a gel container is in a post-disposal position.

The gel capsule 180 may be rotated as described above to translate downward along axis Ia, delivering gel contained within the gel cavity 186 entering the gel delivery channels 165 via the upper apertures 166, traveling through the delivery channels 165, and exiting via the lower apertures 167 onto the skin surface of the patient, such as the patient scalp. A gel capsule 180 in its completed delivery positioning is shown in the capsule assembly 140'' of FIG. 13, whereas the gel capsule 180 of the capsule assembly 140' of FIG. 12 is in a pre-delivery position. The gel may be a conductive gel configured to improve the electrical conductance of brainwave signals to enable performance of an EEG. As shown in FIG. 16, electrode wire 145 may be positioned to be in electrical communication with at least one of gel delivered by the electrode assembly 140 or a structure of the electrode assembly 140 such as one or more of the gel delivery channels 165, one or more of the tip members 180, the flange member 161, or other part. Accordingly, one or more parts of the electrode assembly 140 may be formed of an electrically conductive material. The electrode wire 145 may be connected at another end thereof to the amplifier device 120, as described above.

The electrode assemblies 140 may further comprise a stabilization structure 190, as best shown in FIG. 16. The stabilization structure 190 may be configured to prevent the electrode assemblies 140 from tipping, maintaining a perpendicular or close to perpendicular orientation of the electrode assemblies 140 relative to the skin surface/scalp of the patient. The stabilization structure 190 may comprise a central attachment section 192 and a plurality of leg members 194. The central attachment section 192 may be configured to be attached to the gel delivery structure 160. In the present embodiment, the gel delivery structure 160 comprises an attachment section 191 positioned below the flange member 161, as shown in FIG. 15, and is configured to permit the central attachment structure 162 to be attached thereto. In the present embodiment, the attachment section 191 comprises a deflectable attachment member 195 (also shown in FIG. 12) within which the central attachment structure 162 may be positioned partially within and held thereby. The central attachment section 192 may be annular and define an inner aperture 193 through which the gel delivery channels 165 may be positioned therethrough.

The plurality of leg members 194 may be distributed about a lower surface of the central attachment section 192 and extend downward therefrom. In the current embodiment, the plurality of leg members 194 comprises three leg members positioned radially outward from the longitudinal axis Ia and evenly distributed about the central attachment section 192. It is contemplated and included within the scope of the invention that the plurality of leg members 194 may comprise any number of leg members in any possible distribution. The plurality of leg members 194 may be configured to extend downward from the central attachment section 192 a distance that is determined relative to the position of the lower end of the gel delivery channels 165. In the present embodiment, the plurality of leg members 194 are configured to extend downward a distance such that the lower ends thereof do not extend as far downward as the lower ends of the gel delivery channels, as shown in FIG. 13. Such relative positioning may permit the tip members 168 to come into contact with the skin surface/scalp of the patient, thereby ensuring the complete abrading thereof. It is contemplated and included within the scope of the invention that other embodiments may have one or more of the plurality of leg members 194 extend lower than the gel delivery channels 165 or to the same downward distance thereof. It if further contemplated that the plurality of leg members 194 may extend downward to different distances.

The plurality of leg members may be of sufficient strength and rigidity as to prevent the electrode assemblies 140 from tipping over or collapsing while the EEG headband 100 is being worn, including during placement of the EEG headband 100, during abrading of the scalp and delivery of the gel, and while conducting the EEG analysis.

FIG. 18 is a flowchart illustrating a method of deploying the EEG headband apparatus described herein. The method 1800 may provide a systematic approach for preparing and positioning a headband apparatus according to an embodiment of the invention on a patient to facilitate effective EEG monitoring while ensuring proper electrode contact and gel delivery. While reference is made to the EEG headband apparatus 100 as described above, it is contemplated and included within the scope of the invention that any embodiment of an EEG headband apparatus within the scope of the application may be employed in the method 1800.

At step 1802, the user may remove the EEG headband apparatus 100 from its storage container and inspect the plurality of electrode assemblies 140 to ensure that gel capsules 180 are properly positioned within the capsule receiving structures 141. The user may verify that each gel capsule 180 is in a pre-delivery position where the detent feature 146 engages with the detent interfacing structure 185 to prevent inadvertent rotation during handling.

At step 1804, the user may position the strap member 110 around the head of the patient, ensuring that the plurality of electrode assemblies 140 are aligned with the desired electrode placement locations according to standard EEG positioning protocols, such as the 10-20 system. The elastic properties of the strap member 110 may allow for adjustment to accommodate different head sizes while maintaining appropriate tension for stable positioning.

At step 1806, the user may attach the electrode patch 130 to the forehead of the patient using the adhesive material on the lower surface 132. This attachment may provide additional support for the amplifier device 120 and help stabilize the overall position of the headband apparatus 100 on the patient's head.

At step 1808, the user may activate the amplifier device 120 and establish communication with a remote computerized device to verify proper electrical connectivity through the electrode wires 145. This verification step may ensure that all electrode assemblies 140 are properly connected before proceeding with scalp preparation and gel delivery.

At step 1810, the user may begin scalp preparation by rotating each capsule receiving structure 141 to cause the gel delivery structure 160 to rotate about the central axis Ia. This rotation may cause the tip members 168 of the gel delivery channels 165 to abrade the skin surface of the patient's scalp, removing oils, dead skin cells, and other debris that could interfere with electrical conductivity.

At step 1812, the user may rotate each gel capsule 180 within its respective capsule receiving structure 141 to overcome the resistance provided by the detent feature 146. This rotation may cause the gel capsule 180 to translate downward along the central axis Ia due to the threaded engagement between the threads 143 of the capsule receiving structure 141 and the corresponding threads of the gel capsule 180.

At step 1814, as the gel capsule 180 continues to translate downward, the lower surface 184 may engage with the plurality of teeth members 164 in a sequential manner. The first tooth member 164' may initially pierce the lower surface 184, followed by engagement with the second tooth member 164" as the gel capsule 180 reaches the second longitudinal position. This sequential engagement may reduce the force required for laceration while providing controlled gel release.

At step 1816, the conductive gel contained within the gel cavity 186 may flow through the upper apertures 166 of the gel delivery channels 165, travel through the channels, and exit via the lower apertures 167 onto the prepared skin surface of the patient's scalp. The sloped configuration of the upper wall 163 may direct the gel toward the central portion where the upper apertures 166 are located, ensuring efficient gel delivery.

At step 1818, the user may verify that adequate gel has been delivered to each electrode site and that proper electrical contact has been established between the electrode assemblies 140 and the patient's scalp. The stabilization structure 190 may maintain the perpendicular orientation of each electrode assembly 140 relative to the skin surface throughout this process.

At step 1820, the user may initiate EEG monitoring through the amplifier device 120, which may receive electrical signals from the plurality of electrode assemblies 140 via the electrode wires 145. The amplifier electronics may process these signals and transmit them to the remote computerized device for analysis and recording. The flexible backing member 127 may provide continued support to the amplifier device 120 throughout the monitoring period, conforming to the patient's head contour to maintain comfort and stable positioning.

Some of the illustrative aspects of the present invention may be advantageous in solving the problems herein described and other problems not discussed which are discoverable by a skilled artisan.

While the above description contains much specificity, these should not be construed as limitations on the scope of any embodiment, but as exemplifications of the presented embodiments thereof. Many other ramifications and variations are possible within the teachings of the various embodiments. While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best or only mode contemplated for carrying out this invention, but that the invention will include all embodiments falling within the description of the invention. Also, in the drawings and the description, there have been disclosed exemplary embodiments of the invention and, although specific terms may have been employed, they are unless otherwise stated used in a generic and descriptive sense only and not for purposes of limitation, the scope of the invention therefore not being so limited. Moreover, the use of the terms first, second, etc. do not denote any order or importance, but rather the terms first, second, etc. are used to distinguish one element from another. Furthermore, the use of the terms a, an, etc. do not denote a limitation of quantity, but rather denote the presence of at least one of the referenced item.

What is claimed is:

1. An electroencephalography (EEG) headband apparatus comprising:
   a strap member configured to be removably attachable to a head of a patient;
   an amplifier device attached to the strap member; and
   a plurality of electrode assemblies attached to the strap member; each electrode assembly of the plurality of electrode assemblies comprising:
   a capsule receiving structure having a detent feature configured to resist rotation of a gel capsule positioned there within;
   a stabilization structure comprising:
      a central attachment section; and
      a plurality of leg members positioned radially outward from a central axis of the electrode assembly; and
   a gel delivery structure configured to be positioned at least partially within the capsule receiving structure and to rotatably attach to the stabilization structure such that the gel delivery structure may be able to rotate independently of the stabilization structure, the gel delivery structure comprising:
   a plurality of teeth members configured to engage with and lacerate a lower surface of the gel capsule; and
   a plurality of gel delivery channels configured to deliver gel from the gel capsule to a skin surface of the head of the patient.

2. The EEG headband apparatus of claim 1 wherein the capsule receiving structure comprises a threaded inner surface configured to engage with threads comprised by the gel capsule to facilitate the positioning and attachment of the gel capsule to the capsule receiving structure.

3. The EEG headband apparatus of claim 2 wherein:
   a first tooth of the plurality of teeth members is configured to have a top point thereof at a first longitudinal position;
   a second tooth of the plurality of teeth members is configured to have a top point thereof at a second longitudinal position;
   the first longitudinal position is such that the first tooth engages with the lower surface of the gel capsule before the second tooth; and
   rotation of the gel capsule causes translation of the gel capsule along a central axis of the electrode assembly, thereby causing the lower surface thereof to engage with the first tooth and subsequently engage with the second tooth as the gel capsule translates along the central axis.

4. The EEG headband apparatus of claim 1 wherein the plurality of gel delivery channels each comprise an abrading tip configured to abrade the skin surface of the head of the patient.

5. The EEG headband apparatus of claim 1 wherein a lower end of the plurality of gel delivery channels extends further in a downward direction than a lower end of the plurality of leg members.

6. The EEG headband apparatus of claim 1 wherein the detent feature is a raised section on an inner surface of the capsule receiving structure that is configured to interface with a structure of the gel capsule to resist rotation of the gel capsule.

7. The EEG headband apparatus of claim 1 wherein:
the stabilization structure is fixedly attached to the strap member and comprises an attachment member; and
the gel delivery structure comprises a deflectable attachment member configured to engage with the attachment member of the stabilization structure to rotatably attach the gel delivery structure to the stabilization structure.

8. The EEG headband apparatus of claim 1 further comprising a flexible backing member fixedly attached to the strap member on a side of the strap member opposite a side of the strap member to which the amplifier device is attached and comprising a plurality of backing member attachment members; wherein the amplifier device comprises a plurality of amplifier device attachment members configured to removably attach to the backing member attachment members to removably attach the amplifier device to the flexible backing member, thereby attaching the amplifier device to the strap member.

9. An electroencephalography (EEG) headband apparatus comprising:
a strap member configured to be removably attachable to a head of a patient;
an amplifier device positioned on a first side of the strap member and comprising a plurality of amplifier device attachment members;
a flexible backing member positioned on a second side of the strap member opposite the first side of the strap member and comprising a plurality of backing member attachment members configured to removably attach to the amplifier device attachment members to removably attach the amplifier device to the flexible backing member, thereby attaching the amplifier device and the flexible backing member to the strap member; and
a plurality of electrode assemblies attached to the strap member; each electrode assembly of the plurality of electrode assemblies comprising:
a capsule receiving structure;
a stabilization structure comprising:
a central attachment section; and
a plurality of leg members positioned radially outward from a central axis of the electrode assembly; and
a gel delivery structure configured to be positioned at least partially within the capsule receiving structure and to rotatably attach to the stabilization structure such that the gel delivery structure may be able to rotate independently of the stabilization structure, the gel delivery structure comprising:
a plurality of teeth members configured to engage with and lacerate a lower surface of a gel capsule; and
a plurality of gel delivery channels configured to deliver gel from the gel capsule to a skin surface of the head of the patient.

10. The EEG headband apparatus of claim 9 wherein the capsule receiving structure comprises a threaded inner surface configured to engage with threads comprised by the gel capsule to facilitate the positioning and attachment of the gel capsule to the capsule receiving structure.

11. The EEG headband apparatus of claim 10 wherein:
a first tooth of the plurality of teeth members is configured to have a top point thereof at a first longitudinal position;
a second tooth of the plurality of teeth members is configured to have a top point thereof at a second longitudinal position;

the first longitudinal position is such that the first tooth engages with the lower surface of the gel capsule before the second tooth; and
rotation of the gel capsule causes translation of the gel capsule along a central axis of the electrode assembly, thereby causing the lower surface thereof to engage with the first tooth and subsequently engage with the second tooth as the gel capsule translates along the central axis.

12. The EEG headband apparatus of claim 9 wherein the plurality of gel delivery channels each comprise an abrading tip configured to abrade the skin surface of the head of the patient.

13. The EEG headband apparatus of claim 9 wherein a lower end of the plurality of gel delivery channels extends further in a downward direction than a lower end of the plurality of leg members.

14. The EEG headband apparatus of claim 9 wherein the capsule receiving structure comprises a detent feature configured to resist rotation of a gel capsule positioned therewithin, the detent feature being a raised section on an inner surface of the capsule receiving structure that is configured to interface with a structure of the gel capsule to resist rotation of the gel capsule.

15. The EEG headband apparatus of claim 9 wherein:
the stabilization structure is fixedly attached to the strap member and comprises an attachment member; and
the gel delivery structure comprises a deflectable attachment member configured to engage with the attachment member of the stabilization structure to rotatably attach the gel delivery structure to the stabilization structure.

16. An electroencephalography (EEG) headband apparatus comprising:
a strap member configured to be removably attachable to a head of a patient;
an amplifier device attached to the strap member; and
a plurality of electrode assemblies attached to the strap member; each electrode assembly of the plurality of electrode assemblies comprising:
a capsule receiving structure comprising a threaded inner surface configured to engage with threads comprised by a gel capsule to facilitate positioning and attachment of the gel capsule to the capsule receiving structure;
a stabilization structure comprising:
a central attachment section; and
a plurality of leg members positioned radially outward from a central axis of the electrode assembly; and
a gel delivery structure configured to be positioned at least partially within the capsule receiving structure and to rotatably attach to the stabilization structure such that the gel delivery structure may be able to rotate independently of the stabilization structure, the gel delivery structure comprising:
a plurality of teeth members configured to engage with and lacerate a lower surface of the gel capsule, comprising:
a first tooth of the plurality of teeth members is configured to have a top point thereof at a first longitudinal position; and
a second tooth of the plurality of teeth members is configured to have a top point thereof at a second longitudinal position, the first longitudinal position is such that the first tooth engages with the lower surface of the gel capsule before the second tooth; and a plurality of gel delivery channels configured to deliver gel from the gel capsule to a skin surface of the head of the patient;

wherein rotation of the gel capsule causes translation of the gel capsule along a central axis of the electrode assembly, thereby causing the lower surface thereof to engage with the first tooth and subsequently engage with the second tooth as the gel capsule translates along the central axis.

17. The EEG headband apparatus of claim 16 wherein the plurality of gel delivery channels each comprise an abrading tip configured to abrade the skin surface of the head of the patient.

18. The EEG headband apparatus of claim 16 wherein a lower end of the plurality of gel delivery channels extends further in a downward direction than a lower end of the plurality of leg members.

19. The EEG headband apparatus of claim 16 wherein the capsule receiving structure comprises a detent feature configured to resist rotation of the gel capsule positioned therewithin, the detent feature being a raised section on an inner surface of the capsule receiving structure that is configured to interface with a structure of the gel capsule to resist rotation of the gel capsule.

20. The EEG headband apparatus of claim 16 wherein:

the stabilization structure is fixedly attached to the strap member and comprises an attachment member; and the gel delivery structure comprises a deflectable attachment member configured to engage with the attachment member of the stabilization structure to rotatably attach the gel delivery structure to the stabilization structure.

21. The EEG headband apparatus of claim 16 further comprising a flexible backing member fixedly attached to the strap member on a side of the strap member opposite a side of the strap member to which the amplifier device is attached and comprising a plurality of backing member attachment members; wherein the amplifier device comprises a plurality of amplifier device attachment members configured to removably attach to the backing member attachment members to removably attach the amplifier device to the flexible backing member, thereby attaching the amplifier device to the strap member.

* * * * *